United States Patent

Katano et al.

[11] Patent Number: 5,185,347
[45] Date of Patent: Feb. 9, 1993

[54] PIPERIDINE COMPOUNDS AND ANTIULCER COMPOSITION CONTAINING THE SAME

[75] Inventors: Kiyoaki Katano; Tamako Tomomoto; Hiroko Ogino; Fumiya Hirano; Yasukatsu Yuda; Fukio Konno; Tomoya Machinami; Takashi Tsuruoka; Shigeharu Inoye, all of Kanagawa, Japan

[73] Assignee: Meiji Seika Kaisha Ltd., Tokyo, Japan

[21] Appl. No.: 700,985

[22] Filed: May 16, 1991

[30] Foreign Application Priority Data

May 16, 1990 [JP] Japan ................. 2-124148

[51] Int. Cl.$^5$ ................. C07D 401/12; A61K 31/445
[52] U.S. Cl. ................. 514/322; 514/318; 546/193; 546/194; 546/199
[58] Field of Search ............... 546/194, 199; 514/318, 514/322

[56] References Cited

U.S. PATENT DOCUMENTS 4,045,563 8/1977 Berntsson et al. ............... 546/199

FOREIGN PATENT DOCUMENTS 0045200 3/1982 European Pat. Off. ........... 546/199
0299566 1/1989 European Pat. Off.
0334818 9/1989 European Pat. Off.
3608032 9/1986 Fed. Rep. of Germany.

OTHER PUBLICATIONS

Chemical Abstracts, vol. 106, No. 5, Feb. 2, 1987 (Abstract No. 33 105y).

*Primary Examiner*—C. Warren Ivy
*Assistant Examiner*—Celia Chang
*Attorney, Agent, or Firm*—Sughrue, Mion, Zinn, Macpeak & Seas

[57] ABSTRACT

A piperidine compound represented by formula (I):

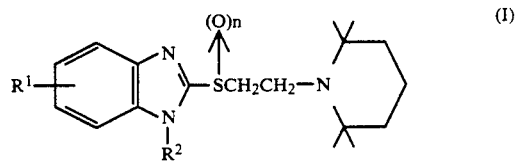

wherein $R^1$ represents a hydrogen atom, a lower alkyl group having from 1 to 4 carbon atoms, a lower alkoxy group having from 1 to 4 carbon atoms, a hydroxymethyl group, $-CO_2R^3$, or

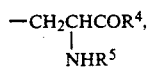

wherein $R^3$ represents a hydrogen atom or a lower alkyl group having from 1 to 4 carbon atoms; $R^4$ represents a hydroxyl group, a lower alkoxy group having from 1 to 4 carbon atoms or $-NR^6R^7$ (wherein $R^6$ and $R^7$, which may be the same or different, each represent a hydrogen atom or a lower alkyl group having from 1 to 4 carbon atoms); and $R^5$ represents a hydrogen atom, a lower alkanoyl group having from 1 to 4 carbon atoms, or a chlorobenzoyl group; $R^2$ represents a hydrogen atom, an alkyl group having from 1 to 4 carbon atoms, a substituted or unsubstituted benzyl group, or a (2,2,6,6-tetramethylpiperidin-1-yl)ethyl group; and n represents 0 or an integer of 1 or 2, and an antiulcer composition containing said piperidine compound.

10 Claims, No Drawings

PIPERIDINE COMPOUNDS AND ANTIULCER COMPOSITION CONTAINING THE SAME

FIELD OF THE INVENTION

This invention relates to piperidine derivatives having antiulcer activity and an antiulcer agent containing at least one of them as an active ingredient, which is effective for treatment or prevention of peptic ulcers such as gastric ulcer and duodenal ulcer.

BACKGROUND OF THE INVENTION

Antiulcer drugs having both functions of suppression of gastric acid secretion and protection of the gastric mucosa have been demanded. Histamine $H_2$ receptor blocking agents typically including cimetidine are drugs which suppress gastric acid secretion. However, these drugs have no action of protecting the gastric mucosa and, in addition, show unfavorable side effects on the central nervous system and, therefore, are not deemed to be sufficient for prevention and treatment of ulcers.

$[H^+\text{-}K^+]$ATPase inhibitors typically including omeprazole powerfully suppress gastric acid secretion but are known to cause anacidity. Besides, they are labile against acids and are susceptible to decomposition by gastric acid.

Accordingly, there has been a need to develop an antiulcer agent which exhibits both suppression of gastric acid secretion and protection of the gastric mucosa in a good balance and is effective on various ulcers, of low toxicity, and stable to gastric acid.

SUMMARY OF THE INVENTION

An object of the present invention is to provide an antiulcer agent which exhibits both suppression of gastric acid secretion and protection of the gastric mucosa in a good balance and is of low toxicity, effective in prevention and treatment of ulcers, and stable to gastric acid.

As a result of extensive investigations, the inventors have found that certain kinds of piperidine compounds possess moderate inhibitory activity on gastric acid secretion and excellent protective properties on the gastric mucosa and exhibit marked inhibitory activity on experimental ulceration of various types.

The present invention relates to a piperidine compound represented by formula (I):

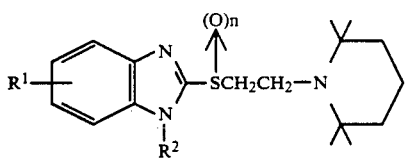

wherein $R^1$ represents a hydrogen atom, a lower alkyl group having from 1 to 4 carbon atoms, a lower alkoxy group having from 1 to 4 carbon atoms, a hydroxymethyl group, $-CO_2R^3$, or

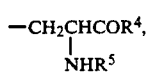

wherein $R^3$ represents a hydrogen atom or a lower alkyl group having from 1 to 4 carbon atoms; $R^4$ represents a hydroxyl group, a lower alkoxy group having from 1 to 4 carbon atoms or $-NR^6R^7$ (wherein $R^6$ and $R^7$, which may be the same or different, each represent a hydrogen atom or a lower alkyl group having from 1 to 4 carbon atoms); and $R^5$ represents a hydrogen atom, a lower alkanoyl group having from 1 to 4 carbon atoms, or a chlorobenzoyl group; $R^2$ represents a hydrogen atom, an alkyl group having from 1 to 4 carbon atoms, benzyl group, or a (2,2,6,6-tetramethylpiperidin-1-yl)ethyl group; and n represents 0 or an integer of 1 or 2.

The present invention also relates to an antiulcer agent useful for treatment and prevention of peptic ulcers, such as gastric ulcer and duodenal ulcer, containing at least one piperidine compound represented by formula (I) as an active ingredient.

DETAILED DESCRIPTION OF THE INVENTION

In formula (I), the lower alkyl group as represented by $R^5$ includes methyl, ethyl, n-propyl, isopropyl, n-butyl, isobutyl, t-butyl, and trifluoromethyl groups. The lower alkoxy group as $R^1$ includes methoxy, ethoxy, propoxy, and 2,2,2-trifluoroethoxy groups. The lower alkyl group as represented by $R^3$ includes methyl, ethyl, n-propyl, isopropyl, n-butyl, isobutyl, and t-butyl groups. The benzyl group as represented by $R^2$ includes benzyl, p-methoxybenzyl, p-nitrobenzyl, and benzhydryl groups. The lower alkyl group as represented by $R^3$, $R^6$, or $R^7$ includes methyl, ethyl, n-propyl, isopropyl, n-butyl, isobutyl, and t-butyl groups. The lower alkoxy group as $R^4$ includes methoxy, ethoxy, propoxy, isopropoxy, n-butoxy, isobutoxy, and t-butoxy groups. The lower alkanoyl group as represented by $R^5$ includes acetyl, propionyl, and n-butyryl groups. The chlorobenzoyl group as $R^5$ includes a benzoyl group and a halogen-substituted benzoyl group (e.g., o-, m- or p-chlorobenzoyl, o-, m- or p-fluorobenzoyl, o-, m- or p-bromobenzoyl). The above-mentioned specific examples of groups are by no means limiting the present invention.

Some of the compounds of formula (I) embrace steric isomers assigned to the carbon atom or sulfur atom thereof and tautomers assigned to the imidazole skeleton thereof. All of these isomers are included in the scope of the present invention.

Of the compounds represented by formula (I), those wherein $R^2$ is a hydrogen atom and n is 0 can be obtained by Process A or B shown below.

Process A:

The compounds of formula (I) wherein $R^3$ is a hydrogen atom and n is 0 can be obtained by reacting a compound represented by formula (II):

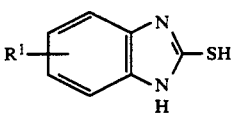

wherein $R^1$ is as defined above, with a compound represented by formula (III):

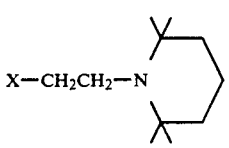

wherein X represents a halogen atom, a tosyloxy group, a trifluoromethanesulfonyloxy group, or a mesyloxy group, in a inert solvent, e.g., N,N-dimethylformamide, dioxane, tetrahydrofuran, water, and ethanol, in the presence of a base such as sodium hydrogencarbonate, potassium hydrogencarbonate, potassium carbonate, sodium carbonate, sodium hydroxide, potassium hydroxide, or a metal hydride (e.g., sodium hydride, potassium hydride) at a temperature of from $-30°$ to $150°$ C., and preferably from $10°$ to $100°$ C. for a period of from 30 minutes to 24 hours. The compound of formula (III) is used at a molar ratio to the compound of formula (II) of 1 to 1.2. The solvent is used in 1 to 100 times weight of the compound of formula (II). The base is used at a molar ratio to the compound of formula (II) of 0.5 to 5.

The compounds of formula (I) wherein $R^3$ is a (2,2,6,6-tetramethylpiperidin-1-yl)ethyl group and n is 0 can be obtained in the same manner as described above by using 2 to 3 equivalents of the compound of formula (III).

Process B:

The compounds of formula (I) wherein $R^3$ is a hydrogen atom and n is 0 can also be obtained by reacting a compound represented by formula (IV):

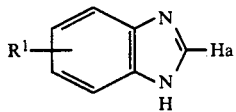

wherein $R^1$ is as defined above; and Ha represents a halogen atom,
with a compound represented by formula (V):

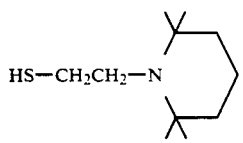

in an inert solvent, e.g., N,N-dimethylformamide, dioxane, tetrahydrofuran, water, and ethanol, in the presence of a base such as sodium hydrogencarbonate, potassium hydrogencarbonate, potassium carbonate, sodium carbonate, sodium hydroxide, potassium hydroxide, or a metal hydride (e.g., sodium hydride, potassium hydride) at a temperature of from $-30°$ to $150°$ C., and preferably from $10°$ to $100°$ C., for a period of from 30 minutes to 24 hours. The compound of formula (V) is used at a molar ratio to the compound of formula (IV) of 1 to 1.2. The amount of the solvent is 1 to 100 times weight of the compound of formula (IV). The base is used at molar ratio to the compound of formula (IV) of 0.5 to 5.

The compounds of formula (I) wherein $R^2$ is a lower alkyl group, a substituted or unsubstituted benzyl group, or a (2,2,6,6-tetramethylpiperidin-1-yl)ethyl group and n is 0 can be obtained by reacting the compound obtained above (formula (I) wherein $R^3=H$; n=0) with a compound represented by formula (VI):

$R^{2'}$-Ha    (VI)

wherein Ha are as defined above; and $R^{2'}$ represents a lower alkyl group, a substituted or unsubstituted benzyl group or a (2,2,6,6-tetramethylpiperidin-1-yl)ethyl group, in an inert solvent, N,N-dimethylformamide, dioxane, tetrahydrofuran, dimethyl sulfoxide, and ethanol, in the presence of a base, e.g., sodium hydrogencarbonate, potassium hydrogencarbonate, potassium carbonate, sodium carbonate, sodium hydroxide, potassium hydroxide, or a metal hydride (e.g., sodium hydride, potassium hydride), at a temperature of from $-30°$ to $150°$ C., and preferably from $10°$ to $100°$ C., for a period of from 30 minutes to 24 hours.

The sulfoxide compounds of formula (I) wherein n is 1 can be obtained by reacting the compound obtained above (formula (I), n=0) with from 1 to 1.2 equivalent of an oxidizing agent in an inert solvent.

In the oxidation reaction, when the oxidizing agent is used in an amount increased by 1 to 1.5 equivalent, the sulfonated compounds of formula (I) wherein n is 2 can be obtained.

The oxidizing agent which can be used includes hydrogen peroxide, m-chloroperbenzoic acid, t-butyl hydroperoxide, N-bromosuccinimide, and manganese dioxide.

The oxidation reaction is preferably carried out by using hydrogen peroxide in acetic acid in the presence of sodium tungstate or by using m-chloroperbenzoic acid in methylene chloride.

The compounds of formula (II) can be synthesized by the process previously proposed by the inventors disclosed in JP-A-2-49774, the term "JP-A" as used herein means an "unexamined published Japanese patent application".

The compounds of formula (IV) can be synthesized by known processes, for example, the process disclosed in JACS II, 3417 (1949).

The desired compound can be recovered from the reaction mixture by extraction with a solvent or precipitation with water. The compound can be further purified by a conventional method such as recrystallization, reprecipitation, silica gel chromatography, adsorption chromatography and the like.

The compounds of the invention may be orally or parenterally administered, with oral administration being preferred. In the case of oral administration, the compound may be administered alone or, if desired, formulated into any desired dose form for oral administration such as tablets, capsules, granules, powders, pills, fine granules or troches. Parenteral administration can be effected by intramuscular, intravenous and subcutaneous injection, percutaneous administration or rectal infusion. The parenteral dose form includes injectable solutions, solutions for rectal infusion, oily or aqueous suppositories and the like.

The antiulcer composition of the present invention can be prepared by mixing the compound with pharmaceutically acceptable carriers such as excipients, extenders, binders, humectants, disintegrating agents, surfactants, lubricants, dispersing agents, buffers, preservatives, dissolving agents, antiseptics, flavors, analgesics and stabilizers using a conventional method. Specific examples of the carriers include lactose, fructose, glucose, starch, gelatin, magnesium carbonate, synthetic magnesium silicate, talc, magnesium stearate, methylcellulose, carboxymethylcellulose and salts thereof, gum arabic, polyethylene glycol, syrup, vaseline, glycerol, ethanol, propylene glycol, citric acid, sodium chloride, sodium sulfite and sodium phosphate.

The content of the compound of the invention in the antiulcer composition is 1 to 70% by weight, preferably 5 to 50% by weight based on the total weight of the composition though it varies depending on the dose form. The method of preparing the composition of the invention is described in Formulation Examples below.

A recommended dosage of the antiulcer composition of the invention is from 0.1 to 100 mg, preferably 0.5 to 50 mg for an adult once or several times per day. The dosage may be vary depending on the mode of administration, the age, distinction of sex and symptom of the patient.

The compounds of formula (I) according to the present invention exhibited antiulcer activity in various ulceration experiments and are therefore useful as treatment agent for peptic ulcers. The antiulcer effect of the compounds of the present invention will be demonstrated below through pharmacological experiments.

1) Test on Water Immersion Restraint Stress-Induced Ulcer:

A 11-week-old Wister male rat having been deprived of food for 18 hours was restrained in a cage and immersed chest-deep in water at 20 to 22° C. for 6 hours to impose a stress. The rat taken out of water was sacrificed by cervical dislocation, the stomach removed, 5 ml of a 5% formalin aqueous solution poured into the stomach, and the whole stomach was soaked in the same solution for 30 minutes. The thus fixed sample was opened along the greater curvature. The longer diameter (mm) of ulcers formed was measured with a slide caliper, and the sum was taken as an ulcer index. Each of test compounds shown in Table 1 below was suspended in a 0.5% carboxymethylcellulose (CMC) solution and administered to the rat (test group) at a dose level of 30 mg/5 ml/kg-b.w. 1 hour before imposition of a stress. Only a 0.5% CMC solution (5 ml) was administered to a control group. A percent inhibition of ulceration was obtained from equation:

Percent Ulceration Inhibition (%) =

$$100 \times \left(1 - \frac{\text{Average Ulcer Index of Test Group}}{\text{Average Ulcer Index of Control Group}}\right)$$

The results obtained are shown in Table 1.

TABLE 1

| Example No. of Test Compound | Percent Inhibition on Ulceration (%) |
|---|---|
| 1 | 92 |
| 2 | 97 |
| 3 | 62 |
| 4 | 40 |
| 5 | 97 |
| 6 | 95 |
| 7 | 97 |
| 8 | 98 |
| 9 | 97 |
| 10 | 100 |
| 11 | 95 |
| 12 | 87 |

2) Ethanol-Induced Ulcer:

A Donryu male rat having been deprived of food for 48 hours and of water for 24 hours orally received 5 ml/kg-b.w. of 100% ethanol. One hour later, the rat was sacrificed in the same manner as described in (1) above, the stomach removed and treated in the same manner as above. The test compound (the compound of Example 2) was suspended in a 0.5% CMC solution and orally administered to the rat at a dose of 30 mg/5 ml/kg-b.w. one hour before administration of ethanol.

Nearly 100% of a control group which received only a 0.5% CMC solution (5 ml) showed erosion, whereas the test group revealed 80% inhibition on erosion, exhibiting an antiulcer effect.

Toxicity:

The compounds of the present invention are of low toxicity. In the case of orally administering the compounds prepared in Examples 1, 2, and 5, $LD_{50}$ of each compound was found to be more than 1 g/kg-b.w.

The present invention is now illustrated in greater detail by way of Examples, but it should be understood that the present invention is not construed as being limited thereto.

EXAMPLE 1

5-Methoxy-2-[2-(2,2,6,6-tetramethylpiperidin-1-yl)ethylthio]benzimidazole

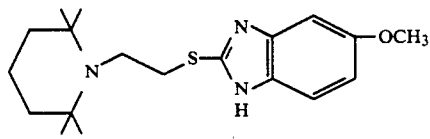

In 15 ml of N,N-dimethylformamide was dissolved 810 mg of 2-mercapto-5-methoxybenzimidazole, and 933 mg of potassium carbonate and 1.62 g of 1-(2-chloroethyl)-2,2,6,6-tetramethylpiperidine hydrochloride were added to the solution, followed by stirring at 65° to 70° C. for 4.5 hours. After completion of the reaction, 200 ml of ethyl acetate and 70 ml of water were added to the reaction mixture, and the thus extracted ethyl acetate layer was washed successively with a diluted sodium hydrogencarbonate aqueous solution and a diluted sodium chloride aqueous solution and dried over anhydrous magnesium sulfate. The extracting solution was removed by distillation under reduced pressure, and the residue was purified by silica gel column chromatography (chloroform:methanol = 50:1 to 25:1 by volume) to obtain 1.25 g (80%) of the titled compound.

$^1$H NMR (CDCl$_3$) δ: 1.15 (12H, s), 1.55–1.75 (6H, m), 3.06 (2H, t), 3.22 (2H, t), 3.85 (3H, s), 6.83 (1H, dd), 7.04 (1H, br. s), 7.41 (1H, br. s)

EI (m/z): 3.48 (M+1)+

EXAMPLE 2

5-[2-(p-Chlorobenzoyl)amino-2-ethoxycarbonyl]ethyl-2-[2,2,6,6-tetramethylpiperidin-1-yl)-ethylthio]benzimidazole

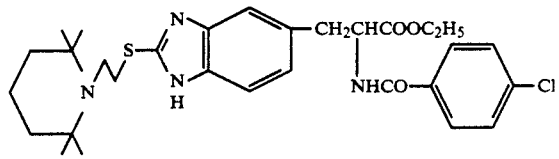

The titled compound was prepared in the same manner as in Example 1 except for using 5-[2-p-chlorobenzoyl)amino-2-ethoxycarbonyl]ethyl-2-mercaptobenzimidazole in place of 2-mercapto-5-methoxybenzimidazole.

$^1$H NMR (CDCl$_3$) δ: 1.14 (12H, s), 1.30 (3H, t), 1.5–1.7 (6H), 3.07 (2H, t), 3.22 (2H, t), 3.37 (2H, d), 4.23

(2H, q), 5.07 (1H, m), 6.58 (1H, br. d), 6.94 (1H, dd), 7.13 (1H, br. s), 7.73 (2H, d), 7.54 (1H, br. s), 7.66 (2H, d)
EI (m/z): 5.71 (M+1)+

EXAMPLE 3

5-[2-Carbamoyl-2-(p-chlorobenzoyl)amino]ethyl-2-[2-(2,2,6,6-tetramethylpiperidin-1-yl)ethylthio]benzimidazole

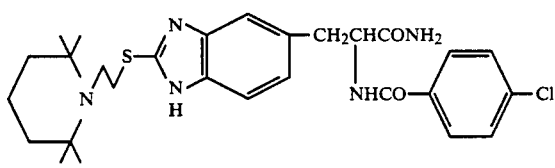

The titled compound was prepared in the same manner as in Example 1 except for using 5-[2-carbamoyl-2-(p-chlorobenzoyl)amino]ethyl-2-mercaptobenzimidazole in place of 2-mercapto-5-methoxybenzimidazole.

$^1$H NMR (CDCl$_3$) δ: 1.13 (12H, s), 1.5.–1.75 (6H), 3.04 (2H, br. s), 3.22 (4H, t), 4.93 (1H, m), 5.70 (1H, br. s), 6.19 (1H, br. s), 7.09–7.14 (2H, m), 7.35 (2H, d), 7.45 (1H, br. s), 7.67 (2H, d)
EI (m/z:) 5.42 (M+1)+

EXAMPLE 4

5-[2-Carboxy-2-(p-chlorobenzoyl)amino]ethyl-2-[2-(2,2,6,6-tetramethylpiperidin-1-yl)ethylthio]benzimidazole

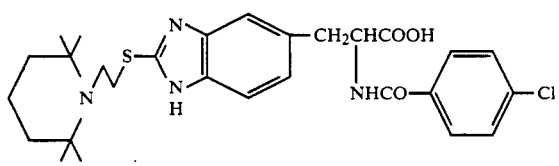

The tilted compound was prepared in the same manner as in Example 1 except for using 5-[2-carboxy-2-(p-chlorobenzoyl)amino]ethyl-2-mercaptobenzimidazole in place of 2-mercapto-5-methoxybenzimidazole.

$^1$H NMR (CDCl$_3$:CD$_3$OD=5:1) δ: 1.28 (12H, s), 1.74 (6H, s), 3.28 (2H, br. s), 3.36 (4H, t), 4.71 (1H, m), 7.06 (1H, d), 7.31 (1H, d), 7.34–7.37 (5H, m), 7.69 (2H, d)
EI (m/z): 543 (M+1)+

EXAMPLE 5

5-[2-Acetylamino-2-ethoxycarbonyl)ethyl-2-[2-(2,2,6,6-tetramethylpiperidin-1-yl)ethylthio]benzimidazole

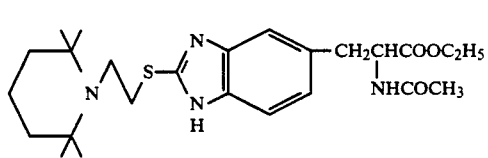

The titled compound was prepared in the same manner as in Example 1 except for using 5-[2-acetylamino-2-ethoxycarbonyl)ethyl-2-mercaptobenzimidazole in place of 2-mercapto-5-methoxybenzimidazole.

$^1$H NMR (CdCl$_3$) δ: 1.16 (12Hs), 1.25 (3H, t), 1.6–1.75 (6H), 1.98 (3H, s), 3.09 (2H, d), 3.23 (4H, t), 4.19 (2H, ABq), 4.89 (1H, m), 5.93 (1H, d), 6.92 (1H, d), 7.12 (1H, br. s), 7.52 (1H, br. s)
EI (m/z): 475 (M+1)+

EXAMPLE 6

5-Methyl-2-[2-(2,2,6,6-tetramethylpiperidin-1-yl)ethylthio]benzimidazole

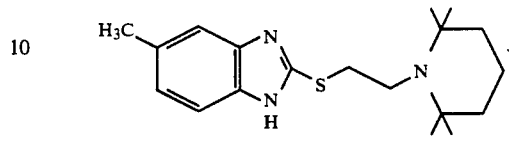

The titled compound was prepared in the same manner as in Example 1 except for using 5-methyl-2-mercaptobenzimidazole in place of 2-mercapto-5-methoxybenzimidazole.

$^1$H NMR (CD$_3$OD) δ: 1.01 (12H, s), 1.42 (4H, t), 1.52–1.57 (2H, m), 2.77 (2H, t), 3.13 (2H, t), 4.85 (3H, s), 7.03 (1H, d), 7.25 (1H, s), 7.34 (1H, d)
EI (m/z): 331 (M+)

EXAMPLE 7

5-Hydroxymethyl-2-[2-(2,2,6,6-tetramethylpiperidin-1-yl)ethylthio]benzimidazole

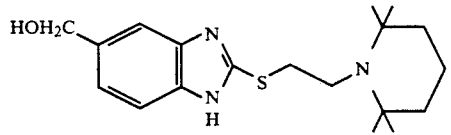

The titled compound was prepared in the same manner as in Example 1 except for using 5-hydroxymethyl-2-mercaptobenzimidazole in place of 2-mercapto-5-methoxybenzimidazole.

$^1$H NMR (CD:OD) δ: 1.05 (12H, s), 1.46 (4H; t), 1.57–1.58 (2H, m), 2.83 (2H, t), 3.19 (2H, t), 4.69 (2H, s), 7.21 (1H, d), 7.44 (1H, d), 7.49 (1H, d)
EI (m/z): 347 (M+)

EXAMPLE 8

5-Methoxycarbonyl-2-[2-(2,2,6,6-tetramethylpiperidin-1-yl)ethylthio]benzimidazole

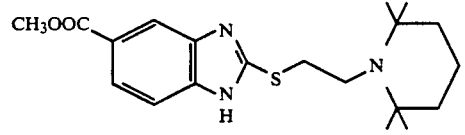

The titled compound was prepared in the same manner as in Example 1 except for using 5-methoxycarbonyl-2-mercaptobenzimidazole in place of 2-mercapto-5-methoxybenzimidazol.

$^1$H NMR (CD:OD) δ: 1.07 (12H, s), 1.45 (4H, t), 1.55–1.60 (2H, m), 2.85 (2H, t), 3.24 (2H, t), 3.92 (3H, s), 7.49 (1H, d), 7.89 (1H, d), 8.13 (1H, s)
EI (m/z): 376 (M+1)+

EXAMPLE 9

2-[(2,2,6,6-Tetramethylpiperidin-1-yl)ethylthio1-1H-benzimidazole

The titled compound was prepared in the same manner as in Example 1 except for using 2-mercaptobenzimidazole in place of 2-mercapto-5-methoxybenzimidazole.

$^1$H NMR (CDCl$_3$) δ: 1.16 (12H, s), 1.64 (4H, m), 1.72 (2H, m), 3.08 (2H, t), 3.26 (2H, t), 7.18 (2H, m), 7.53 (2H, br. s)

EI (m/z): 318 (M+1)$^+$

EXAMPLE 10

1-Methyl-[2-(2,2,6,6-tetramethylpiperidin-1-yl)ethylthiolbenzimidazole

In 5 ml of N,N-dimethylformamide was dissolved 200 mg of the compound obtained in Example 9, and 30.4 mg of 60% sodium hydride was added to the solution, followed by stirring for about 1 hour. To the mixture was added 0.48 ml of iodomethane, and the mixture was allowed to react at room temperature for 2 hours. The reaction mixture was extracted with 300 ml of chloroform, and the chloroform layer was washed with a saturated sodium chloride aqueous solution and dried over anhydrous magnesium sulfate. The residue was freed of the solvent by distillation under reduced pressure, and the resulting viscous brown liquid was purified by silica gel column chromatography (chloroform:methanol=50:1 to 10:1 by volume) to obtain 202 mg (97%) of the titled compound as a pale yellow powder.

$^1$H NMR (CDCl$_3$) δ: 1.08 (12H, s), 1.42 (4H, t), 1.52 (2H, m), 2.83 (2H, t), 3.28 (2H, t), 3.70 (3H, s), 7.21 (3H, m), 7.63 (1H, m)

EI (m/z): 332 (M+1)$^+$

EXAMPLE 11

1-Benzyl-[2-(2,2,6,6-tetramethylpiperidin-1-yl)ethylthiolbenzimidazole

The titled compound was synthesized in the same manner as in Example 10, except for replacing iodomethane with benzyl bromide.

$^1$H NMR (CDCl$_3$) δ: 1.07 (12H, s), 1.41 (4H, t), 1.52 (2H, m), 2.82 (2H, m), 3.29 (2H, m), 5.32 (2H, s), 7.13–7.21 (4H, m), 7.27–7.33 (2H, m), 7.36 (1H, m), 7.66 (1H, d)

EI (m/z): 408 (M+1)$^+$

EXAMPLE 12

5(6)-(2-Acetylamino-2-ethoxycarbonyl)ethyl-1-[2-(2,2,6,6-tetramethylpiperidin-1-yl)]ethyl-2-[2-(2,2,6,6-tetramethylpiperidin-1-yl)ethylthio]benzimidazole (5-/6-position mixture)

The titled compound was synthesized in the same manner as in Example 5, except for using 2.5 equivalents of 1-(2-chloroethyl)-2,2,6,6-tetramethylpiperidine.

$^1$H NMR (CDCl$_3$) δ: 1.15–1.30 (24H), 1.23 and 1.28 (tx2, 3H), 1.40–1.60 (12H), 1.98 and 1.99 (sx2, 3H), 2.74 (d, d., 2H), 2.84 (d, d., 2H), 3.21–3.32 (4H, m), 3.95–4.03 (2H, m), 4.11–4.23 (2H, m), 4.88 (1H, m), 5.90 (1H, m), 6.92 (1H, m), 6.98 and 7.34 (1H, dx2), 7.15 and 7.52 (1H, dx2)

FORMULATION EXAMPLE 1

Tablet:
The following components are mixed together well and punched out to obtain 1,000 tablets.

| | |
|---|---|
| Compound of Example 1 | 2.5 g |
| lactose | 12 g |
| 6% HPC lactose | 8 g |
| potato starch | 2 g |
| magnesium stearate | 0.5 g |
| total weight | 25 g |

FORMULATION EXAMPLE 2

Capsule:
The following components are mixed together well and charged in hard capsules to obtain 1,000 capsules.

| | |
|---|---|
| Compound of Example 1 | 2.5 g |
| lactose | 18 g |
| potato starch | 4 g |
| maqnesium stearate | 0.5 g |
| total weight | 25 g |

FORMULATION EXAMPLE 3

Injection:
The following amounts of the compound of Example 1 and glucose are dissolved in distilled water for injection and make the total volume 1,000 ml. The resulting solution is filtered with a glass filter and the filtrate is dispensed in 1 ml portion into an ampule to obtain 1,000 ampules.

| Compound of Example 1 | 0.5 g |
| --- | --- |
| glucose | 7 g |
| distilled water for injection | adequate amount |
| total volume | 1,000 ml |

While the invention has been described in detail and with reference to specific examples thereof, it will be apparent to one skilled in the art that various changes and modifications can be made therein without departing from the spirit and scope thereof.

What is claimed is:

1. A piperidine compound represented by formula (I):

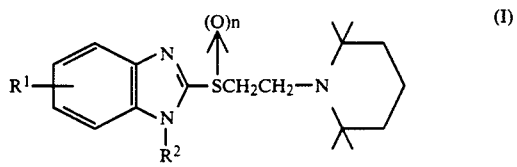

wherein $R^1$ represents a hydrogen atom, a lower alkyl group having from 1 to 4 carbon atoms, a lower alkoxy group having from 1 to 4 carbon atoms, a hydroxymethyl group, —$CO_2R^3$, or

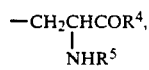

wherein $R^3$ represents a hydrogen atom or a lower alkyl group having from 1 to 4 carbon atoms; $R^4$ represents a hydroxyl group, a lower alkoxy group having from 1 to 4 carbon atoms or —$NR^6R^7$ (wherein $R^6$ and $R^7$, which may be the same or different, each represent a hydrogen atom or a lower alkyl group having from 1 to 4 carbon atoms); and $R^5$ represents a hydrogen atom, a lower alkanoyl group having from 1 to 4 carbon atoms, or a chlorobenzoyl group; $R^2$ represents a hydrogen atom, an alkyl group having from 1 to 4 carbon atoms, a benzyl group, or a (2,2,6,6-tetramethylpiperidin-1-yl)ethyl group; and n represents 0 or an integer of 1 or 2.

2. An antiulcer composition containing as an active ingredient at least one piperidine compound represented by formula (I):

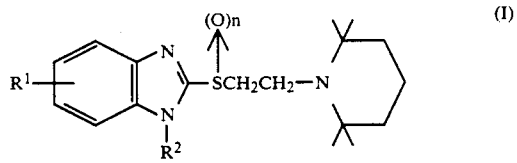

wherein $R^1$ represents a hydrogen atom, a lower alkyl group having from 1 to 4 carbon atoms, a lower alkoxy group having from 1 to 4 carbon atoms, a hydroxymethyl group, —$CO_2R^3$, or

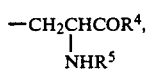

wherein $R^3$ represents a hydrogen atom or a lower alkyl group having from 1 to 4 carbon atoms; $R^4$ represents a hydroxyl group, a lower alkoxy group having from 1 to 4 carbon atoms or —$NR^6R^7$ (wherein $R^6$ and $R^7$, which may be the same or different, each represent a hydrogen atom or a lower alkyl group having from 1 to 4 carbon atoms); and $R^5$ represents a hydrogen atom, a lower alkanoyl group having from 1 to 4 carbon atoms, or a chlorobenzoyl group; $R^2$ represents a hydrogen atom, an alkyl group having from 1 to 4 carbon atoms, a benzyl group, or a (2,2,6,6-tetramethylpiperidin-1-yl)ethyl group; and n represents 0 or an integer of 1 or 2, and a pharmaceutically acceptable carrier.

3. 5-Methoxy-2-[2-(2,2,6,6-tetramethylpiperidin-1-yl)ethylthio]benzimidazole.

4. 5-(2-Acetylamino-2-ethoxycarbonyl)ethyl-2-[2-(2,2,6,6-tetramethylpiperidin-1-yl)ethylthio]benzimidazole.

5. 5-Methoxycarbonyl-2-[2-(2,2,6,6-tetramethylpiperidin-1-yl)ethylthio]benzimidazole.

6. 5(6)-(2-Acetylamino-2-ethoxycarbonyl)ethyl-1-[2-(2,2,6,6-tetramethylpiperidin-1-yl)]ethyl-2-[2-(2,2,6,6-tetramethylpiperidin-1-yl)ethylthio]benzimidazole.

7. An antiulcer composition according to claim 2, wherein said piperidine compound is 5-methoxy-2-[2-(2,2,6,6-tetramethylpiperidin-1-yl)ethylthio]benzimidazole.

8. An antiulcer composition according to claim 2, wherein said piperidine compound is 5-(2-acetylamino-2-ethoxycarbonyl)ethyl-2-[2-(2,2,6,6-tetramethylpiperidin-1-yl)ethylthio]benzimidazole.

9. An antiulcer composition according to claim 2, wherein said piperidine compound is 5-methoxycarbonyl-2-[2-(2,2,6,6-tetramethylpiperidin-1-yl)ethylthio]benzimidazole.

10. An antiulcer composition according to claim 2, wherein said piperidine compound is 5(6)-(2-acetylamino-2 -ethoxycarbonyl)ethyl-1-[2-(2,2,6,6-tetramethylpiperidin-1-yl)]ethyl-2-[2(2,2,6,6-tetramethylpiperidin-1-yl)ethylthio]benzimidazole.

* * * * *